(12) United States Patent
Pranaitis et al.

(10) Patent No.: US 10,729,348 B2
(45) Date of Patent: Aug. 4, 2020

(54) HIGH DENSITY MAPPING AND ABLATION CATHETER

(71) Applicant: St. Jude Medical, Cardiology Division, Inc., St. Paul, MN (US)

(72) Inventors: Simon Pranaitis, Sammamish, WA (US); Claude Rickerd, Bloomington, MN (US); Gregory Olson, Elk River, MN (US)

(73) Assignee: St. Jude Medical, Cardiology Division, Inc., St. Paul, MN (US)

( * ) Notice: Subject to any disclaimer, the term of this patent is extended or adjusted under 35 U.S.C. 154(b) by 271 days.

(21) Appl. No.: 15/559,140

(22) PCT Filed: May 6, 2016

(86) PCT No.: PCT/US2016/031105
§ 371 (c)(1),
(2) Date: Sep. 18, 2017

(87) PCT Pub. No.: WO2016/182876
PCT Pub. Date: Nov. 17, 2016

(65) Prior Publication Data
US 2018/0064359 A1    Mar. 8, 2018

Related U.S. Application Data

(60) Provisional application No. 62/159,891, filed on May 11, 2015.

(51) Int. Cl.
*A61B 18/14* (2006.01)
*A61B 5/042* (2006.01)
(Continued)

(52) U.S. Cl.
CPC .......... *A61B 5/0422* (2013.01); *A61B 5/0408* (2013.01); *A61B 5/6852* (2013.01);
(Continued)

(58) Field of Classification Search
CPC ........ A61B 18/1492; A61B 2018/0016; A61B 2018/00351; A61B 2018/00577;
(Continued)

(56) References Cited

U.S. PATENT DOCUMENTS 4,660,571 A * 4/1987 Hess .................... A61B 5/0422
604/105
5,156,151 A * 10/1992 Imran .................... A61N 1/056
600/375

(Continued)

FOREIGN PATENT DOCUMENTS

JP    2002-143178    5/2002
JP    2007-244857    9/2007

(Continued)

OTHER PUBLICATIONS

International Search Report and Written Opinion for PCT/US2016/031105, dated Jul. 26, 2016.

*Primary Examiner* — Michael F Peffley
(74) *Attorney, Agent, or Firm* — Wiley Rein LLP (57) ABSTRACT

A high density mapping and ablation catheter includes a tip electrode positioned at its distal end and a plurality of electrodes (e.g., ring electrodes, ring-segment electrodes, spot electrodes, and/or printed traces) disposed proximally of the tip electrode within the distal region. A plurality of conductors extending through the elongate catheter body electrically connect the tip electrode and other electrodes to a source of ablation energy, an electrophysiology mapping device, and/or a programmable electric stimulator. A switching circuit can be employed, for example to enable a practitioner to selectively activate certain electrodes for ablation, for electrophysiological mapping, for pacing, or to deactivate certain electrodes entirely.

22 Claims, 4 Drawing Sheets

(51) Int. Cl.
*A61B 5/00* (2006.01)
*A61N 1/05* (2006.01)
*A61B 5/0408* (2006.01)
*A61N 1/362* (2006.01)
*A61B 18/00* (2006.01)

(52) U.S. Cl.
CPC ............ *A61B 18/1492* (2013.01); *A61N 1/05* (2013.01); *A61N 1/056* (2013.01); *A61N 1/362* (2013.01); *A61B 2018/0016* (2013.01); *A61B 2018/00351* (2013.01); *A61B 2018/00577* (2013.01); *A61B 2018/00702* (2013.01); *A61B 2018/00839* (2013.01); *A61B 2018/1467* (2013.01); *A61B 2018/1497* (2013.01); *A61B 2562/0209* (2013.01); *A61B 2562/043* (2013.01)

(58) Field of Classification Search
CPC ........... A61B 2018/00702; A61B 2018/00839; A61B 2018/1467; A61B 2018/1497; A61B 2562/0209; A61B 2562/043; A61B 5/0408; A61B 5/0422; A61B 5/6852; A61N 1/05; A61N 1/056; A61N 1/362
See application file for complete search history.

(56) References Cited

U.S. PATENT DOCUMENTS

| | | | | |
|---|---|---|---|---|
| 5,239,999 | A | | 8/1993 | Imran |
| 5,450,846 | A | * | 9/1995 | Goldreyer ............ A61B 5/0422 600/374 |
| 5,545,200 | A | * | 8/1996 | West .................. A61B 18/1492 606/29 |
| 5,938,694 | A | * | 8/1999 | Jaraczewski ......... A61B 5/0422 607/122 |
| 8,050,732 | B2 | * | 11/2011 | Desai .................. A61B 5/0422 600/374 |
| 9,480,525 | B2 | * | 11/2016 | Lopes ................. A61B 5/6858 |
| 9,757,191 | B2 | * | 9/2017 | Avitall ............... A61B 18/1492 |
| 2008/0281391 | A1 | | 11/2008 | Macadam |
| 2010/0204692 | A1 | | 8/2010 | Stewart et al. |

FOREIGN PATENT DOCUMENTS

| | | |
|---|---|---|
| JP | 2007-537831 | 12/2007 |
| JP | 08-505547 | 2/2008 |
| JP | 2008-539901 | 11/2008 |
| JP | 41545216 | 7/2010 |
| JP | 11-503644 | 1/2011 |
| WO | 96/32897 | 10/1996 |
| WO | 2006/121883 | 11/2006 |

* cited by examiner

HIGH DENSITY MAPPING AND ABLATION CATHETER

CROSS-REFERENCE TO RELATED APPLICATION

This application claims the benefit of U.S. provisional application No. 62/159,891, filed 11 May 2015, which is hereby incorporated by reference as though fully set forth herein.

BACKGROUND

The instant disclosure relates to medical devices. In particular, the instant disclosure relates to multi-electrode catheters that are usable for both tissue ablation and electrophysiological mapping.

Catheters are used in a variety of diagnostic and therapeutic procedures, for example to diagnose and/or treat conditions such as atrial and ventricular arrhythmias. For example, a catheter carrying one or more electrodes can be deployed and manipulated through a patient's vasculature and, once located at the intended site, radiofrequency ("RF") energy can be delivered through the electrodes to ablate tissue. Multi-electrode catheters can also be used to generate cardiac geometries/model surfaces and/or electrophysiology maps.

Various extant multi-electrode catheters can have certain specific advantages and shortcomings. For example, ablation catheters often have improved steerability relative to catheters used for electrophysiology mapping, making them well-suited for accessing hard-to-reach areas. Yet, because they have a relatively small number of widely-spaced electrodes (that is, they are relatively low density), they are not as well-suited to gathering electrophysiology data.

Electrophysiology mapping catheters, on the other hand, typically have a higher density of electrodes (e.g., 10-20 electrodes with various inter-electrode spacing), making them well-suited to gathering electrophysiology data, but less maneuverable and less well-suited to the delivery of therapy (e.g., ablation).

Because of these tradeoffs, extant devices generally are not used to perform multiple functions, potentially requiring multiple devices to be inserted into and removed from a patient's body during a single procedure. For example, during an electrophysiology procedure, a high density multi-electrode catheter may be used to generate an electrophysiology map. Once the map is created, the high density mapping catheter can be removed and an RF ablation catheter inserted in its place.

Yet, many practitioners would find it advantageous, for example, to conduct additional electrophysiology assessments (e.g., isochronal activation maps, geometry creation, lesion/scar quality assessments, and the like), both during and after the ablation (e.g., to judge the efficacy of the ablation), and it would be efficient to do so with the same catheter that was used to deliver the ablation in the first instance. It would also be advantageous to use more highly-maneuverable ablation catheters to map the electrophysiological activity in hard-to-reach areas, but without compromising the speed with which electrophysiology maps can be generated when using high density multi-electrode catheters.

BRIEF SUMMARY

Disclosed herein is a high density mapping and ablation catheter, including: an elongate catheter body having a distal region; a tip electrode positioned at a distal end of the distal region; a plurality of electrodes disposed proximally of the tip electrode within the distal region; a plurality of conductors extending through the elongate catheter body, at least one conductor of the plurality of conductors electrically connected to the tip electrode and at least one conductor of the plurality of conductors respectively electrically connected to each electrode of the plurality of electrodes; and at least one connector configured for connection to a source of ablation energy, an electrophysiology mapping device, and a programmable electric stimulator, wherein the plurality of conductors are electrically connected to the at least one connector such that: the tip electrode can be electrically coupled to the source of ablation energy, thereby to deliver ablation energy to a tissue, the electrophysiology mapping device, thereby to measure electrophysiological activity in the tissue, and the programmable electric stimulator, thereby to apply a pacing stimulus to the tissue, and each electrode of the plurality of electrodes can be electrically coupled to the electrophysiology mapping device, thereby to measure electrophysiological activity in the tissue, and the programmable electric stimulator, thereby to apply a pacing stimulus to the tissue. According to aspects of the disclosure, the plurality of conductors are also electrically connected to the at least one connector such that a subset of the plurality of electrodes can also be electrically coupled to the source of ablation energy, thereby to deliver ablation energy to the tissue.

The plurality of electrodes can include a plurality of ring electrodes and/or a plurality of ring-segment electrodes. In embodiments disclosed herein, the plurality of electrodes can also include a plurality of spot electrodes. In still other embodiments disclosed herein, the plurality of electrodes includes a plurality of printed electrodes, such as a plurality of conductive traces. Likewise, the tip electrode can include a plurality of discrete electrode segments.

The plurality of electrodes can be uniformly spaced along the distal region of the elongate catheter body; according to aspects of the disclosure, the plurality of electrodes and the tip electrode can be uniformly spaced along the distal region of the elongate catheter body.

It is also contemplated that the plurality of electrodes are spaced along the distal region of the elongate catheter body such that at least one pair of adjacent electrodes of the plurality of electrodes is sufficiently closely spaced to provide meaningful measurements of the electrophysiological activity in the tissue. According to aspects of the instant disclosure, the plurality of electrodes are spaced along the distal region of the elongate catheter body such that each pair of adjacent electrodes of the plurality of electrodes is sufficiently closely spaced to provide meaningful measurements of the electrophysiological activity in the tissue.

The at least one connector can include: a first connector configured for connection to the source of ablation energy; a second connector configured for connection to the electrophysiology mapping device; and a third connector configured for connection to the programmable electric stimulator.

Also disclosed herein is a combined electrophysiology mapping and ablation system including: a source of ablation energy; an electrophysiology mapping device; and a catheter. The catheter can include: an elongate catheter body having a distal region; a tip electrode positioned at a distal end of the distal region; a plurality of electrodes disposed proximally of the tip electrode within the distal region; and a plurality of conductors configured to electrically connect the tip electrode to both the source of ablation energy and the electrophysiology mapping device such that the tip electrode is operable both to deliver ablation energy to a tissue and to measure electrophysiological activity from the tissue, and to electrically connect each electrode of the plurality of electrodes to the electrophysiology mapping device such that each electrode of the plurality of electrodes is operable to measure electrophysiological activity from the tissue. The plurality of conductors can also be configured to electrically connect a subset of the plurality of electrodes to the source of ablation energy such that the subset of the plurality of electrodes is also operable to deliver ablation energy to the tissue.

A switching circuit is also disclosed, which is operable to selectively couple the tip electrode and each electrode of the plurality of electrodes to one of the source of ablation energy and the electrophysiology mapping device. The switching circuit can operate according to a user-specified program or according to a preset program.

In embodiments, the system further includes a programmable electric stimulator. The plurality of conductors can thus be further configured to electrically connect the tip electrode to the programmable electric stimulator, such that the tip electrode is further operable to apply a pacing stimulus to the tissue. Likewise, the plurality of conductors can be further configured to electrically connect each electrode of the plurality of electrodes to the programmable electric stimulator, such that each electrode of the plurality of electrodes is further operable to apply a pacing stimulus to the tissue.

The instant disclosure also provides a high density mapping and ablation catheter including: an elongate catheter body having a distal region; and a plurality of electrodes disposed within the distal region of the elongate catheter body, the plurality of electrodes including a tip electrode positioned at a distal end of the elongate catheter body, wherein the tip electrode is configured to be connected to a source of ablation energy, thereby to deliver ablation energy to a tissue, and to a programmable electric stimulator, thereby to apply a pacing stimulus to the tissue; wherein the plurality of electrodes are configured to be connected to an electrophysiology mapping device and to the programmable electric stimulator; and wherein the plurality of electrodes are spaced sufficiently close to each other such that at least one pair of adjacent electrodes of the plurality of electrodes is sufficiently closely spaced to provide meaningful measurements of electrophysiological activity in the tissue. For example, the plurality of electrodes can be spaced sufficiently close to each other such that at least two pairs of adjacent electrodes of the plurality of electrodes are sufficiently closely spaced to provide meaningful measurements of electrophysiological activity in the tissue.

At least some electrodes of the plurality of electrodes can be configured to be connected to the source of ablation energy, thereby to deliver ablation energy to the tissue.

The plurality of electrodes can also be user-programmable for connection to the electrophysiology mapping device.

The foregoing and other aspects, features, details, utilities, and advantages of the present invention will be apparent from reading the following description and claims, and from reviewing the accompanying drawings.

DETAILED DESCRIPTION

Figure 1:
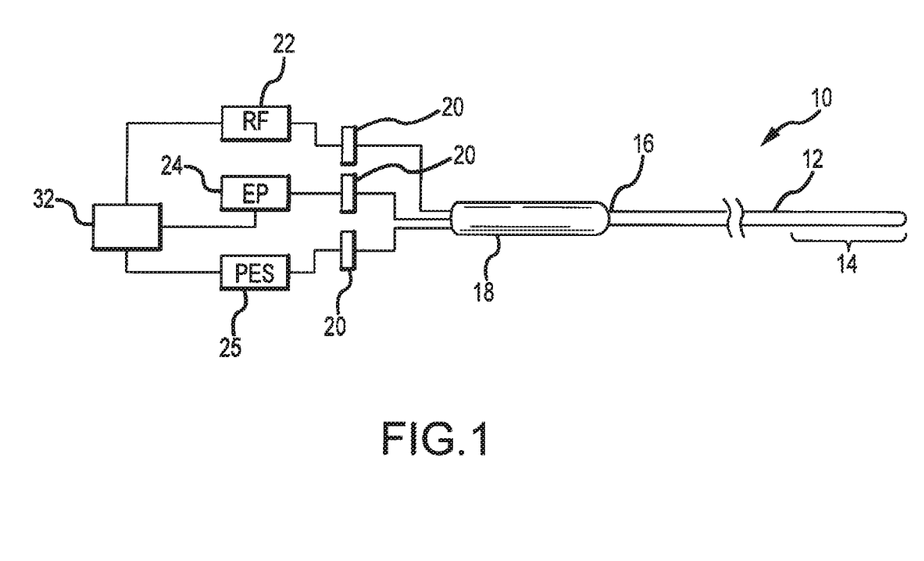
FIG. 1 shows a representative high density multi electrode mapping and ablation catheter according to an embodiment of the teachings herein.

FIG. 1 shows a high density multi-electrode mapping and ablation catheter 10. Catheter 10 generally includes an elongate catheter body 12 having a distal region 14 and a proximal end 16. A handle 18 is shown coupled to proximal end 16.

Also shown in FIG. 1 are connectors 20. Connectors 20 are configured to be connected to a source of ablation energy (schematically illustrated as RF source 22, which can be, for example, the Ampere™ RF ablation generator of St. Jude Medical, Inc.), an electrophysiology mapping device (schematically illustrated as 24, which can be, for example, the EnSite™ Velocity™ cardiac mapping system, also of St. Jude Medical, Inc.), and a programmable electrical stimulator (schematically illustrated as 25, which can be, for example the EP-4™ cardiac stimulator, also of St. Jude Medical, Inc.). Although FIG. 1 depicts three separate connectors 20, it is within the scope of the instant disclosure to have a combined connector 20 that is configured for connection to two or more of RF source 22, electrophysiology mapping device 24, and programmable electrical stimulator 25.

Various additional aspects of the construction of catheter 10 will be familiar to those of ordinary skill in the art. For example, the person of ordinary skill in the art will recognize that catheter 10 can be made steerable, for example by incorporating an actuator into handle 18 that is coupled to one or more steering wires that extend through elongate catheter body 12 and that terminate in one or more pull rings within distal region 14. Likewise, the ordinarily skilled artisan will appreciate that catheter 10 can be an irrigated catheter, such that it can also be coupled to a suitable supply of irrigation fluid and/or an irrigation pump. As a further example, those of ordinary skill in the art will appreciate that catheter 10 can be equipped with force feedback capabilities.

Insofar as such features are not necessary to an understanding of the instant disclosure, they are neither illustrated in the drawings nor explained in detail herein. By way of example only, however, catheter 10 can incorporate various aspects and features the following catheters, all from St. Jude Medical, Inc.: the EnSite™ Array™ catheter; the FlexAbility™ ablation catheter; the Safire™ BLU™ ablation catheter; the Therapy™ Cool Path™ irrigated ablation catheter; the Livewire™ TC ablation catheter; and the TactiCath™ Quartz irrigated ablation catheter.

Figure 2:
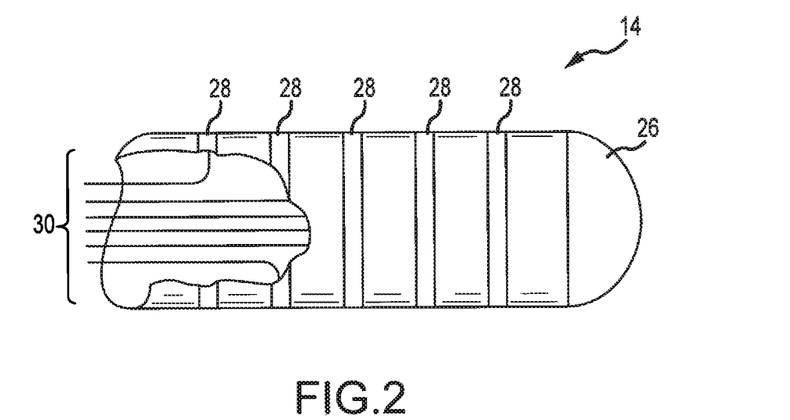
FIG. 2 is a close up view of the distal region of the catheter shown in FIG. 1. Portions of the exterior of the catheter body have been cut away in order to reveal the interior thereof.
Figure 3:
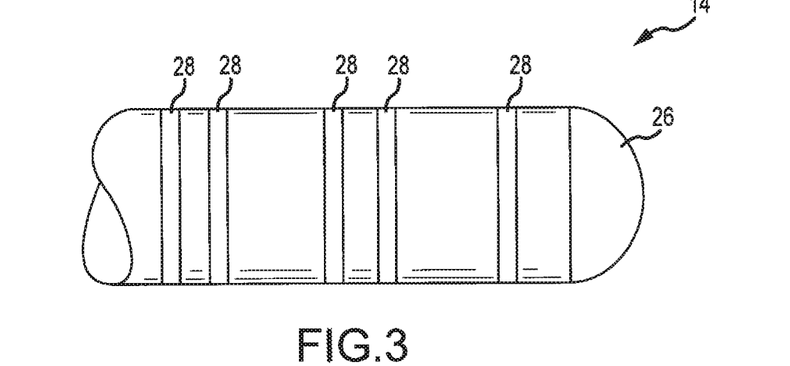
FIG. 3 is a close up view of another embodiment of the distal region of the catheter shown in FIG. 1.

FIG. 2 is a close-up view of distal region 14, with a portion of the exterior of catheter body 12 cut away to show the interior thereof. Distal region 14 includes a tip electrode 26 positioned at its distal end and a plurality of additional electrodes 28 proximal of tip electrode 26. The most proximal of electrodes 28 will, in certain embodiments, be no more than about 10 mm from the distal tip of distal region 14, but it is contemplated that it can be more proximally located (e.g., in some embodiments, up to about 24 mm from the distal tip of distal region 14, or, in other embodiments, up to about 31 mm from the distal tip of distal region 14).

FIG. 2 depicts five ring electrodes 28, each of which is about 1 mm wide, with an inter-electrode spacing of about 1 mm. In other aspects of the disclosure, ring electrodes 28 can be as narrow as about 0.5 mm and as close together as about 0.75 mm spacing, which would allow for about eight ring electrodes 28 within distal region 14.

From the disclosure herein, the person of ordinary skill in the art will understand and appreciate that, by varying the size and spacing of electrodes 28, different diagnostic and/or therapeutic objectives and/or outcomes can be achieved. For example, the ordinarily skilled artisan will appreciate that, as electrodes 28 become smaller and closer together, the electrograms collected thereby will become sharper and more localized evidencing better depiction of local, near-field depolarization of the cardiac tissue in contact with the electrodes. Thus, it should be understood that distal region 14 can include any number of such electrodes 28 and that the inter-electrode spacing need not always be 1 mm. In some embodiments, in fact, the inter-electrode spacing can vary along the length of distal region 14. To this end, several additional representative embodiments of distal region 14 are described below.

Also shown in FIG. 2 are a plurality of conductors 30 that extend through elongate catheter body 12. At least one conductor 30 is electrically connected to tip electrode 26, and at least one conductor 30 is respectively electrically connected to each electrode 28. That is, according to certain aspects of the disclosure, there is at least a one-to-one correspondence between conductors 30 and electrodes 26, 28. Of course, in other embodiments, there can be a one-to-many (i.e., a single conductor 30 that is electrically connected to more than one electrode 26, 28) or many-to-one correspondence (i.e., multiple conductors 30 connected to any individual electrode 26, 28) between conductors 30 and electrodes 26, 28.

The opposite ends of conductors 30 (i.e., the ends thereof that are not electrically connected to electrodes 26, 28) are electrically connected to connectors 20. Thus, when connectors 20 are connected to RF source 22, electrophysiology mapping device 24, and programmable electric stimulator 25, tip electrode 26 is electrically coupled to RF source 22, electrophysiology mapping device 24, and, in aspects of the disclosure, programmable electric stimulator 25. As such, tip electrode 26 is operable to deliver ablation energy to a tissue, to measure electrophysiological activity in the tissue, and/or to apply pacing stimuli to the tissue.

Similarly, electrodes 28 are electrically coupled to electrophysiology mapping device 24 and, in aspects of the disclosure, additionally to programmable electric stimulator 25, such that electrodes 28 are operable to measure electrophysiological activity in the tissue and to apply pacing stimuli to the tissue. It is also contemplated that at least some of electrodes 28 can also be coupled to RF source 22 via conductors 30 and connectors 20, such that there are at least some electrodes 28 that are also operable to deliver ablation energy to the tissue.

Stated another way, tip electrode 26 is operable in multiple modes (e.g., ablation, mapping, and pacing), while electrodes 28 are operable at least in a mapping mode and, in some embodiments, also in a pacing mode and/or an ablation mode. Indeed, in certain embodiments, the function(s) of electrodes 26, 28 can be programmable, for example via a switching circuit 32 (shown schematically in FIG. 1). Switching circuit 32 can operate according to a preset program and/or according to a user-defined program, the latter of which allows a practitioner to specify which of electrodes 26, 28 operate in an ablation mode, which operate in a mapping mode, which operate in a pacing mode, and which are inoperative. This affords practitioners a high degree of customization of the pattern of mapping, ablation, pacing, and inactive electrodes within distal region 14 in order to achieve various diagnostic and/or therapeutic objectives and outcomes.

In addition to providing programmable control over the function of electrodes 26, 28 in order to virtually change their configuration, various physical configurations of electrodes 26, 28 are also contemplated. For example, as discussed above, FIG. 2 shows a single, solid tip electrode 26 and five evenly-spaced ring electrodes 28. This arrangement has certain advantages. For example, it allows for better wave propagation assessment during EGM timing assessments. It also facilitates denser imaging display resolution during voltage mapping. An additional advantage is that evenly-spaced electrodes are less likely to miss the "edge" of a lesion during lesion assessment.

FIGS. 3-7 depict alternative physical configurations of electrodes 26, 28. For example, in FIG. 3, ring electrodes 28 have staggered spacing (that is, they are not uniformly distributed through distal region 14). In general, however, at least some pairs of adjacent electrodes 28 in FIG. 3 remain close enough to each other to be usable to measure electrophysiological activity in the tissue. By comparison to extant ablation catheters, where the inter-electrode spacing (e.g., so-called 2-5-2 or 1-4-1 spacing) results in distances that are too great to make meaningful bipolar electrophysiology measurements, the catheters disclosed herein equalize the "window" of timing physical locations, better enabling practitioners to analyze the propagation of the cardiac activation wavefront.

Figure 4:
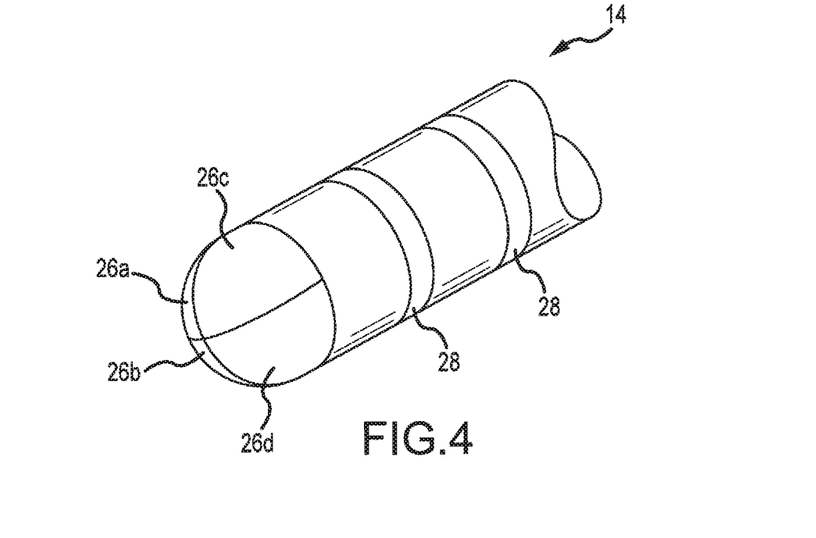
FIG. 4 depicts a tip electrode according to another embodiment disclosed herein.

As another example, FIG. 4 depicts an embodiment of catheter 10 where tip electrode 26 comprises a plurality of discrete electrode segments 26a, 26b, 26c, and 26d. This effectively quadruples the number of electrodes at the distal end of distal region 14 without requiring additional physical "landscape" on catheter 13.

Figure 5A:
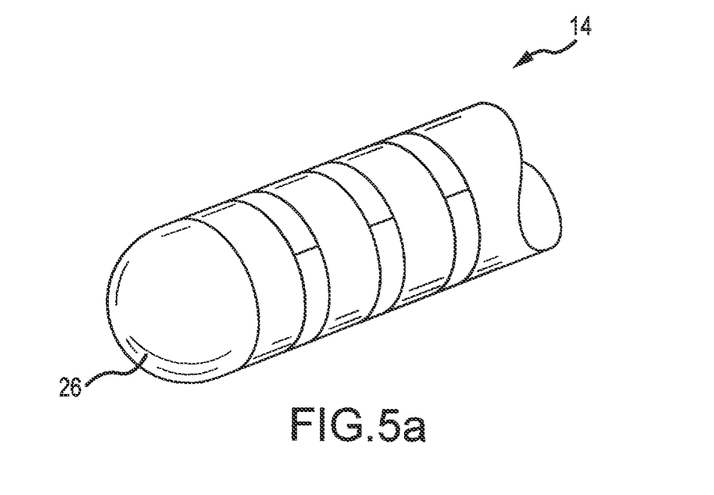
FIGS. 5a and 5b depict additional configurations of the distal region of a multi-electrode catheter as disclosed herein.
Figure 5B:
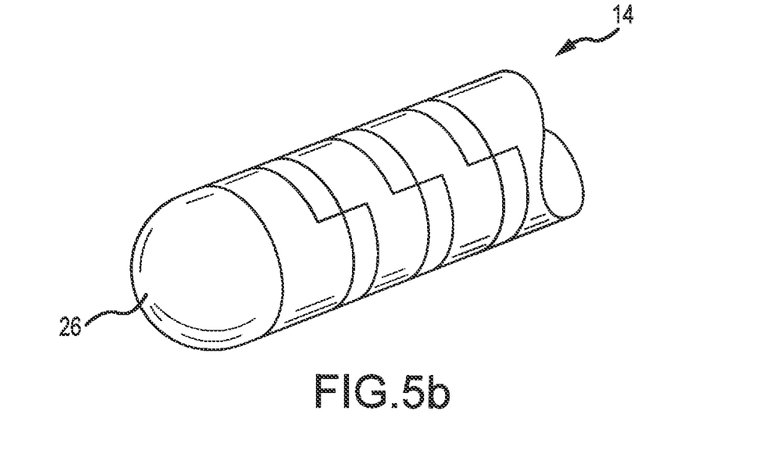

As shown in FIGS. 5a and 5b, electrodes 28 can also be segmented to increase the number of electrodes within distal region 14 with no increase in the required physical "landscape." FIG. 5a shows an embodiment where ring electrodes 28 are only segmented; FIG. 5b shows a further variation where ring electrodes 28 are both segmented and axially staggered. Other patterns and arrangements are also contemplated as within the scope of this disclosure.

The various physical patterns of electrodes 26, 28 contemplated herein (including segmented electrodes 26, 28) can be achieved in numerous ways. For example, electrodes of the desired shape could be bonded to elongate catheter body 12 using techniques known to those of ordinary skill in the art. Ring segments could also be created by bonding full ring electrodes and then covering portions thereof with an insulating material.

Figure 6:
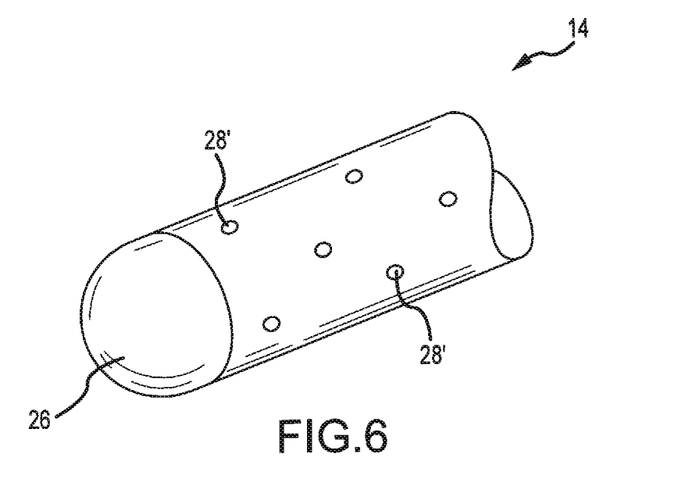
FIG. 6 depicts still another embodiment of the distal region of a multi-electrode catheter as disclosed herein.
Figure 7:
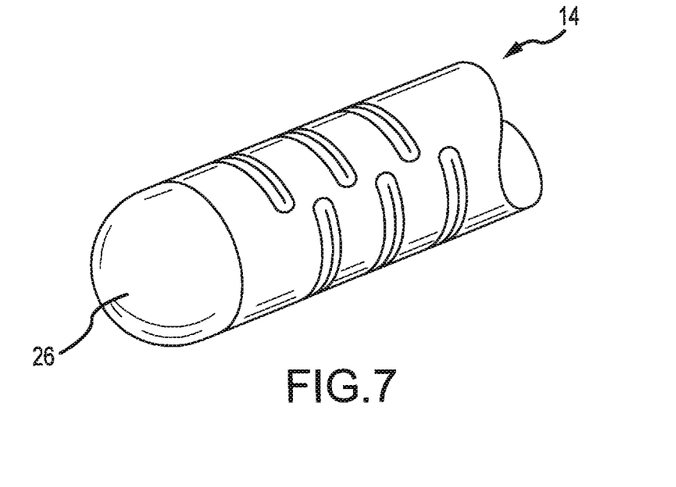
FIG. 7 illustrates yet another embodiment of the distal region of a multi-electrode catheter as disclosed herein.

Yet another embodiment of distal region 14 is shown in FIG. 6. FIG. 6 employs spot electrodes 28' rather than ring electrodes 28. In some embodiments, spot electrodes 28' can be printed on to elongate catheter body 12, for example using a conductive ink. A similar printing process can also be used to form conductive trace electrodes (shown, for example, in FIG. 7). Moreover, printed traces can be used to electrically connect electrodes 26, 28 to conductors 30; in some embodiments, printed traces could replace some or all of conductors 30. In fact, the use of printed electrodes increases not only the number of electrodes 28 within distal region 14, but also allows for highly complex and complicated physical patterns of electrodes 28.

For purposes of measuring electrophysiological activity, electrodes 26, 28 can operate in either a unipolar or a bipolar mode; the choice may be left to the practitioner. Referring again to the embodiment shown in FIG. 2, for example, electrophysiological activity can be measured using six unipolar electrodes or five pairs of bipolar electrodes.

As discussed above, this increase in the number of measurement points for electrophysiological activity is advantageous because it substantially reduces the amount of time required to generate an electrophysiology map using an ablation catheter. For example, over approximately ten minutes, an extant ablation catheter (having a tip electrode and three more proximal ring electrodes, and thus a total of four unipolar electrodes) being used to gather electrophysiology data might sample several hundred electrophysiology data points; only a fraction of those may be viable for use in an electrophysiology map. The high density catheters illustrated in FIG. 2 (having a tip electrode and five more proximal ring electrodes spaced more closely together), on the other hand, can sample over 1000 data points within the same time period. Even if only a fraction of those points are suitable for use in an electrophysiology map, it remains the case that a relatively small increase in the number of electrodes (or bipolar electrode pairs) on an ablation catheter can triple the number of data points collected in a given time/reduce the time required to perform electrophysiological mapping by ⅔.

Although several embodiments of this invention have been described above with a certain degree of particularity, those skilled in the art could make numerous alterations to the disclosed embodiments without departing from the spirit or scope of this invention.

All directional references (e.g., upper, lower, upward, downward, left, right, leftward, rightward, top, bottom, above, below, vertical, horizontal, clockwise, and counterclockwise) are only used for identification purposes to aid the reader's understanding of the present invention, and do not create limitations, particularly as to the position, orientation, or use of the invention. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other.

It is intended that all matter contained in the above description or shown in the accompanying drawings shall be interpreted as illustrative only and not limiting. Changes in detail or structure may be made without departing from the spirit of the invention as defined in the appended claims.

What is claimed is:

1. A high density mapping and ablation catheter, comprising:
   an elongate catheter body having a distal region, the distal region including a first arcuate surface and a second arcuate surface opposite and adjacent the first arcuate surface, wherein the first and second arcuate surfaces together define a circumferential surface of the distal region;
   a tip electrode positioned at a distal end of the distal region;
   a plurality of electrodes disposed proximally of the tip electrode within the distal region, the plurality of electrodes comprising a first group of electrodes positioned entirely within the first arcuate surface and a second group of electrodes positioned entirely within the second arcuate surface;
   a plurality of conductors extending through the elongate catheter body, at least one conductor of the plurality of conductors electrically connected to the tip electrode and at least one conductor of the plurality of conductors respectively electrically connected to each electrode of the plurality of electrodes; and
   at least one connector configured for connection to a source of ablation energy, an electrophysiology mapping device, and a programmable electric stimulator,
   wherein the plurality of conductors are electrically connected to the at least one connector such that:
     the tip electrode can be electrically coupled to the source of ablation energy, thereby to deliver ablation energy to a tissue, the electrophysiology mapping device, thereby to measure electrophysiological activity in the tissue, and the programmable electric stimulator, thereby to apply a pacing stimulus to the tissue, and
     each electrode of the plurality of electrodes can be electrically coupled to the electrophysiology mapping device, thereby to measure electrophysiological activity in the tissue, and the programmable electric stimulator, thereby to apply a pacing stimulus to the tissue.

2. The catheter according to claim 1, wherein the plurality of conductors are electrically connected to the at least one connector such that a subset of the plurality of electrodes can also be electrically coupled to the source of ablation energy, thereby to deliver ablation energy to the tissue.

3. The catheter according to claim 1, wherein the plurality of electrodes comprises a plurality of ring-segment electrodes.

4. The catheter according to claim 1, wherein the plurality of electrodes comprises a plurality of spot electrodes.

5. The catheter according to claim 1, wherein the plurality of electrodes comprises a plurality of printed electrodes.

6. The catheter according to claim 5, wherein the plurality of printed electrodes comprises a plurality of conductive traces.

7. The catheter according to claim 1, wherein the plurality of electrodes are uniformly spaced along the distal region of the elongate catheter body.

8. The catheter according to claim 7, wherein the plurality of electrodes and the tip electrode are uniformly spaced along the distal region of the elongate catheter body.

9. The catheter according to claim 1, wherein the plurality of electrodes are spaced along the distal region of the elongate catheter body such that at least one pair of adjacent electrodes of the plurality of electrodes is sufficiently closely spaced to provide meaningful measurements of the electrophysiological activity in the tissue.

10. The catheter according to claim 9, wherein the plurality of electrodes are spaced along the distal region of the elongate catheter body such that each pair of adjacent electrodes of the plurality of electrodes is sufficiently closely spaced to provide meaningful measurements of the electrophysiological activity in the tissue.

11. The catheter according to claim 1, wherein the tip electrode comprises a plurality of discrete electrode segments.

12. The catheter according to claim 1, wherein the at least one connector comprises:
- a first connector configured for connection to the source of ablation energy;
- a second connector configured for connection to the electrophysiology mapping device; and
- a third connector configured for connection to the programmable electric stimulator.

13. A combined electrophysiology mapping and ablation system, comprising:
- a source of ablation energy;
- an electrophysiology mapping device; and
- a catheter, comprising:
  - an elongate catheter body having a distal region, the distal region including a first arcuate surface and a second arcuate surface opposite and adjacent the first arcuate surface, wherein the first and second arcuate surfaces together define a circumferential surface of the distal region;
  - a tip electrode positioned at a distal end of the distal region;
  - a plurality of electrodes disposed proximally of the tip electrode within the distal region, the plurality of electrodes comprising a first group of electrodes positioned entirely within the first arcuate surface and a second group of electrodes positioned entirely within the second arcuate surface; and
  - a plurality of conductors configured to electrically connect the tip electrode to both the source of ablation energy and the electrophysiology mapping device such that the tip electrode is operable both to deliver ablation energy to a tissue and to measure electrophysiological activity from the tissue, and to electrically connect each electrode of the plurality of electrodes to the electrophysiology mapping device such that each electrode of the plurality of electrodes is operable to measure electrophysiological activity from the tissue.

14. The system according to claim 13, wherein the plurality of conductors are further configured to electrically connect a subset of the plurality of electrodes to the source of ablation energy such that the subset of the plurality of electrodes is also operable to deliver ablation energy to the tissue.

15. The system according to claim 14, further comprising a switching circuit operable to selectively couple the tip electrode and each electrode of the plurality of electrodes to one of the source of ablation energy and the electrophysiology mapping device.

16. The system according to claim 15, wherein the switching circuit operates according to a user-specified program.

17. The system according to claim 15, wherein the switching circuit operates according to a preset program.

18. The system according to claim 13, further comprising a programmable electric stimulator, and wherein:
- the plurality of conductors are further configured to electrically connect the tip electrode to the programmable electric stimulator, such that the tip electrode is further operable to apply a pacing stimulus to the tissue; and
- the plurality of conductors are further configured to electrically connect each electrode of the plurality of electrodes to the programmable electric stimulator, such that each electrode of the plurality of electrodes is further operable to apply a pacing stimulus to the tissue.

19. A high density mapping and ablation catheter, comprising:
- an elongate catheter body having a distal region, the distal region including a first arcuate surface and a second arcuate surface opposite and adjacent the first arcuate surface, wherein the first and second arcuate surfaces together define a circumferential surface of the distal region; and
- a plurality of electrodes disposed within the distal region of the elongate catheter body, the plurality of electrodes including a tip electrode positioned at a distal end of the elongate catheter body, a first group of electrodes positioned entirely within the first arcuate surface, and a second group of electrodes positioned entirely within the second arcuate surface,
- wherein the tip electrode is configured to be connected to a source of ablation energy, thereby to deliver ablation energy to a tissue, and to a programmable electric stimulator, thereby to apply a pacing stimulus to the tissue;
- wherein the plurality of electrodes are configured to be connected to an electrophysiology mapping device and to the programmable electric stimulator; and
- wherein the plurality of electrodes are spaced sufficiently close to each other such that at least one pair of adjacent electrodes of the plurality of electrodes is sufficiently closely spaced to provide meaningful measurements of electrophysiological activity in the tissue.

20. The catheter according to claim 19, wherein the plurality of electrodes are spaced sufficiently close to each other such that at least two pairs of adjacent electrodes of the plurality of electrodes are sufficiently closely spaced to provide meaningful measurements of electrophysiological activity in the tissue.

21. The catheter according to claim 19, wherein at least some electrodes of the plurality of electrodes are configured to be connected to the source of ablation energy, thereby to deliver ablation energy to the tissue.

22. The catheter according to claim 19, wherein the plurality of electrodes are user-programmable for connection to the electrophysiology mapping device.

* * * * *